United States Patent [19]
Minion et al.

[11] Patent Number: 5,821,059
[45] Date of Patent: Oct. 13, 1998

[54] MYCOPLASMA EXPRESSION SYSTEM

[75] Inventors: F. Chris Minion, Ames, Iowa; Kevin L. Knudtson, Salt Lake City, Utah

[73] Assignee: Iowa State University Research Foundation, Inc., Ames, Iowa

[21] Appl. No.: 592,406

[22] PCT Filed: Aug. 6, 1993

[86] PCT No.: PCT/US93/07407

§ 371 Date: May 23, 1996

§ 102(e) Date: May 23, 1996

[87] PCT Pub. No.: WO95/04830

PCT Pub. Date: Feb. 16, 1995

[51] Int. Cl.$^6$ .............................. C12Q 1/02; C12N 1/21; C12N 15/10; C12N 15/11
[52] U.S. Cl. .................. 435/6; 435/69.1; 435/172.3; 435/252.3; 435/320.1; 536/24.1
[58] Field of Search .............................. 435/320.1, 172.3, 435/252.3, 6, 69.1; 536/24.1

[56] References Cited

FOREIGN PATENT DOCUMENTS 2076903  2/1993  Canada .

OTHER PUBLICATIONS

Loechel et al., Nucleic Acids Research 19 (24): 6905–6912 (1991).

Mahairas et al., "Random Insertion of the Gentamicin Resistance Transposon Tn4001 In Mycoplasma Pulmonis", *Plasmid*, vol. 21:43–47, (1989).

Mahairas et al., "Development of A Cloning System In Mycoplasma Plumonis", *Gene,* vol. 93:61–65, (1990).

Dybvig, "Transformation of Acholeplasma Laidlawii With Streptococcal Plasmids pVA868 and pVA920", *Plasmid,* vol. 21:155–160, (1989).

Gafney et al., "Promoters of Mycoplasma Capricolum Ribosomal RNA Operons: Identical Activities But Different Regulation In Homologous And Heterologous Cells", *Nucl. Acids, Res.,* vol. 16:61–76, (1988).

Rodriguez et al., "A Survey of Molecular Cloning Vectors and Their Uses", *Vectors,* Butterworths, pp. 153–177, (1988).

*Primary Examiner*—Johnny F. Railey, II
*Attorney, Agent, or Firm*—Foley & Lardner

[57] ABSTRACT

A system for identifying mycoplasma regulatory sequences with protein fusion constructs has been developed. This system has identified mycoplasma regulatory sequences that can be used in expression vectors. The expression vectors employing these mycoplasma regulatory sequences permit the expression of foreign DNA sequences in mycoplasma hosts, such as Acholeplasma.

21 Claims, 13 Drawing Sheets

FIG. 1A

| Bacterial Strain or plasmid | Relevant genotype and phenotype |
|---|---|
| *E. coli* | |
| DH5α | φ80dlacZΔM15 endA1 recA1 hsdR17 supE44 thi-1 gyrA relA1 F⁻ Δ(lacZYA argF)U169 |
| CSH50 | ara Δ(lac-pro) strA thi F⁻ |
| χ289 | F⁻ supE42 λ⁻ T3ʳ |
| *Acholeplasma* | |
| ISM1499 | laboratory isolate |
| ISM1503 | ISM1499::pISM1007 |
| ISM1520 | ISM1499::pISM1026 Tcʳ |
| ISM2050 | ISM1520::pISM2050 Gmʳ Tcʳ |
| ISM2050.1 | ISM1520::pISM2050.1 Gmʳ Tcʳ |
| ISM2050.2 | ISM1520::pISM2050.2 Gmʳ Tcʳ |
| ISM2050.8 | ISM1520::pISM2050.8 Gmʳ Tcʳ |
| ISM2050.18 | ISM1520::pISM2050.18 Gmʳ Tcʳ |
| ISM2050.25 | ISM1520::pISM2050.25 Gmʳ Tcʳ |
| ISM2050.69 | ISM1520::pISM2050.69 Gmʳ Tcʳ |
| ISM2050.70 | ISM1520::pISM2050.70 Gmʳ Tcʳ |

FIG. 1B

| Plasmids | |
|---|---|
| pDIA15 | *trp'-lacZYA* $Kan^r$ |
| pMC1871 | |
| pISM1003 | $Gm^r$ $Ap^r$ |
| pISM2002 | pISM1003 with *M. capricolum rrnA* P2 promoter $Gm^r$ $Ap^r$ |
| pISM2003 | pISM1003 with *E. coli rrnB* P1 promoter $Gm^r$ $Ap^r$ |
| pISM2004 | pISM1003 with *trp-lacZYA* $Gm^r$ $Ap^r$ |
| pISM2005 | pISM2002 with *trp-lacZYA* $Gm^r$ $Ap^r$ |
| pISM2006 | pISM2003 with *trp-lacZYA* $Gm^r$ $Ap^r$ |
| pISM2009 | pISM2004 with *E. coli rrnB* P1 promoter containing 700 bp of the upstream region of the *M. capricolum rrnB* P2 promoter $Gm^r$ $Ap^r$ |
| pISM2010 | pISM2004 with *M. capricolum rrnA* P2 promoter containing 700 bp of the upstream region of the *M. capricolum rrnB* P2 promoter $Gm^r$ $Ap^r$ |
| pISM2011 | pISM2010 with promoter in reverse orientation $Gm^r$ $Ap^r$ |
| pISM2050 | Promoterless *lacZ* fusion vector $Gm^r$ $Ap^r$ |
| pISM2050.1 | pISM2050 with 2.8 kb of ISM1499 DNA $Gm^r$ $Ap^r$ |
| pISM2050.2 | pISM2050 with 0.9 kb of ISM1499 DNA $Gm^r$ $Ap^r$ |
| pISM2050.8 | pISM2050 with 1.0 kb of ISM1499 DNA $Gm^r$ $Ap^r$ |
| pISM2050.18 | pISM2050 with 0.9 kb of ISM1499 DNA $Gm^r$ $Ap^r$ |
| pISM2050.25 | pISM2050 with 0.8 kb of ISM1499 DNA $Gm^r$ $Ap^r$ |
| pISM2050.69 | pISM2050 with 2.5 kb of ISM1499 DNA $Gm^r$ $Ap^r$ |
| pISM2050.70 | pISM2050 with 2.3 kb of ISM1499 DNA $Gm^r$ $Ap^r$ |
| pISM2083 | 1.6 kb *ClaI-HindIII* fragment containing the 0.9 kb chromosomal insert from pISM2050.2 and the first 800 bp of the promoterless *lacZ* gene from pMC1971 cloned into pSP71 |

FIG. 4

| Strain | ß-gal levels Units ± SD | lacZ transcript levels counts/vol. |
| --- | --- | --- |
| ISM1499 | 0 | 66,517 |
| ISM1520 | 0 | 112,580 |
| ISM2050 | 1 ± 1 | 77,006 |
| ISM2050.1 | 17 ± 4 | 387,036 |
| ISM2050.2 | 1,428 ± 100 | 1,941,175 |
| ISM2050.8 | 48 ± 15 | 246,890 |
| ISM2050.18 | 48 ± 6 | 595,954 |
| ISM2050.25 | 211 ± 26 | 661,166 |
| ISM2050.69 | 350 ± 71 | 1,054,501 |
| ISM2050.70 | 186 ± 120 | 803,629 |
| CSH50 | 1 ± 1 | Not Done |
| χ289 | 5,382 ± 453 | Not Done |

FIG. 5

| Source of Promoter | -35 | | -10 | | rbs | |
|---|---|---|---|---|---|---|
| pISM2050.1 | TCACTGCACC--TGAAGAACTACATAAATATAAACTTGAAGAA | . 49bp . | CAAGAATTGCTAATG |
| pISM2050.2 | TATCTTCCTT-TAATTACTATTATATAGTATAATATAAAAGT | . 10bp . | TTGGAGTGATAAGATG |
| pISM2050.8 | TTACGCTACAATCTAAAACCCAAATTGGTCAAGTACATGCTGAA | . 4bp . | TTAGTGCACAAACACTGATG |
| pISM2050.18 | AGAATTCATGCTTAAATCACCTTTATATTTAAATAATCCATCAGT | . 3bp . | CAAAGGTTTAGAACAAATG |
| pISM2050.25 | ATTGTTGATGTATTCATACATGATATATATACGCGAAAGTGTTGAGGAATACAAATG |
| pISM2050.69 | TAGTAATAGATCCCGTTTACACTCATGATAATATAGTAGGGG | . 19bp . | TGTGAAGTCAATG |
| pISM2050.70 | GGGTTCGATTGATAATGAATTTACAAGATATTTGGACATAACGTTTTTCTATG |
| Consensus | TtcAtn | 16 to 18 bp | TATAaW | | | |
| E. coli consensus | TTGACW | 16 to 18 bp | TAtAaT | | | |

FIG. 6

```
                CCA GTG GNC CTC ATN CTG AGT ATG AAA AAC TCC CAA ATC TTG GTC AAG NAG
                                 10              19              28              37              46

GTA CNT TAT TAT TAG TAT CTG ACT CTA CCA ATN CTG AAC AAG AAG GTT TGA NTC AAT
             61              70              79              88              97             106

CTG AAT CTA AAG TTG GTA AAT CCA TTA ACG AAC TCT TCA CAA GAA TTC CAG GAC GTA
            118             127             136             145             154             163

TTA TTA TTG CAA CCT TTG CAT CCA ACT TGT ATC GAA TTC AAC AAA TTA TTG AAG CAT
            175             184             193             202             211             220

CTG AAT TAA CAG GTA GAA AAG TTG CTG TTT TTG GAC GTT CTA TGG AAC GTG CTA TTG
            232             241             250             259             268             277
                                                                                         -35
AGG CTG GAC AAC AAT CAG GCT ATA TTA AAC CTA GAA AAG GTA CAT TCA CTG CAC CTG
            289             298             307             316             325             334
                                       *
AAG AAC TAC ATA AAT ATA AAC TTG AAG AAA CTT GTA TTT TGG TTA CTG GTT CCC AAG
            346             355             364             373             382             391
                        -10
                                       rbs               start
                                                   Met Asp Pro Val Val
GTG AAC CAC TTG CAG CAT TAT CAA GAA TTG CTA ATG GAT CCC GTC GTT TT
            403             412             421             430             439
```

FIG. 7

```
            GTC TTG GAT GAA GTC TTA AAG CAC CAC CGA TAC CTG AAT TAA TCC
                         11              20              29              38              47

CAT ATT TTC TTG CTT TAT AAC TTG CAG TTG ATA TAA CAC CTC TTG CAT ATG AGG ATT
             62              71              80              89              98             107

GTC CTC CAA CAA CAA AAA CCT TGT TTT TAA GGT AAG GTT CTT TAA GTA TCG CGC ATG
            119             128             137             146             155             164

TTG CAA AGA ACG CAT TTA AGT CGA TAT GAA AAA TAA TTT TAG CCG TTT TTT TCA TCA
            176             185             194             203             212             221

TTA TCT TCC TTT AAT TAC TAT ATA GTA TAA TAT AAA AAG TAT AAG ATT ATT TGG                rbs
            233             242             251             260             269             278
rbs                                                   -10                                    
                  start
                  Met Ala Gln Asn Lys Thr Ala Thr Lys Glu Lys Ala Val Lys Pro Ala
AGT GAT AAG ATG GCA CAA AAT AAG ACA GCA ACA AAA GAA AAG GCA GTA AAG CCT GCT
            290             299             308             317             326             335
       -35
Lys Lys Glu Ser Leu Val Phe Lys Asp Pro Val Val
AAA AAA GAA TCT TTA GTA TTT AAA GAT CCC GTC GTT TT
            347             356             365             374
```

FIG. 8

```
        CGA GTA AGT AAC ATT AAC TAT GTA ACA ACA TCC TTA GCA ATT GTC AAA
         10              19          28          37          46

GAT AAT GAT TTC GCA ATT GTA GAA TCA TTT AAA CGA GAG GTT ATG TAA TTT ATC CAA
         61          70          79          88          97         106

ACA TTT AAA GGC ATT GNG GTC TCC AGT GGA GTT GCA ATT CCA AAA ATA CAT CAC TTA
        118         127         136         145         154         163

GCT GAA ACC ACT CAG ATG AGC TTA AAA AAG TTT TCA ACG GAT AAA AAT GTT GAA CTT
        175         184         193         202         211         220
                                                                      -35
AAT CGT TTT AAT GAA ACG ATT AAA GAA GCT GTT TCT CAA TTA GAA TTA CTT ACG CTA
        232         241         250         259         268         277

CAA TCT AAA ACC GAA ATT GGT CAA GTA CAT GCT GAA ATC TTT AGT GCA CAA ACA CTG
        289         298         307         316         325         334
                           -10              *         rbs
start
Met Leu Lys Asp Pro Val Val
ATG TTA AAA GAT CCC GTC GTT TT
                    355
        346
```

FIG. 9

```
     AGT AGN ATC ACT CAA CCA ATA ATN NTT GAA GTC TCT NAA NCC AGT TTT GAA
                  10          19          28          37          46

TAT GTG AAT ACN CNA NAC ATT ATN NAA GAT GCT AAT ATT CCA AGA GGG TCT TTT TAC
              61          70          79          88          97         106

CAG TAC TTT GAA GAT AAG NCG GAT ATG TAT GAA TAT ATC ATG GAT TAT ATT AGT TCA
             118         127         136         145         154         163

ATA AAA AGA TAT TTT AAA AGT ATA TTT GAA GCA GTG AAT CTG AAT TTT ATA GAG
             175         184         193         202         211         220

CGA ATA GAG GCA ATT TAT TTA GCG GGT GTA AAA TTT AAG TCC GAG AAC CCT GAT TTT
             232         241         250         259         268         277
                              -35

GTA AGA GCA GGA GAA TTC ATG CTT AAA TCA CCT TTA TAT TTA AAT AAT CCA TCA GTA
             289         298         307         316         325         334
                              -10                       *
   rbs                 start
                       Met Ile Ser Ile Tyr Glu Ser Trp Ile Ile Asn Asp Pro
NCC AAA GGT TTA GAA CAA ATG ATT ATT TCA TAC GAG TCT TGG ATT ATC AAT GAT CCC
             346         355         364         373         382         391
```

FIG. 10

```
                AAG TTT TTT TAT CAC TTT GAC TTT GAA CTC TTC TGC TTG TCT ATT TCA TTG
                                 11          20              29          38          47
-35
                                                 -10                          rbs         start
                                                                                           Met Lys Tyr
ATG TAT TCA TAC ATG ATA TAA TAT ATA CGC GAA AGT TGA GGA ATA CAA ATG AAA TAC
 62              71          80              89              98         107

Leu Val Gly Thr Tyr Thr Lys Asn Leu Ser Glu Gly Ile Tyr Leu Val Asp Glu Asp
TTA GTT GGC ACT TAT ACT AAA AAT CTA TCC GAA GGT ATT TAC TTA GTT GAT GAG GAT
119             128         137             146             155         164

Lys Val Ser Leu His Met Arg Leu Phe Asn Pro Thr Tyr Phe Thr Leu Gln Glu Gly
AAA GTC TCT TTA CAT ATG AGA TTA TTT AAT CCA ACT TAT TTT ACT TTA CAA GAA GGT
176             185         194             203             212         221

His Leu Phe Thr Ile Ala Arg Gly Gly Ile Glu Ile Tyr Gln Asp
CAT TTA TTT ACA ATT GCT AGA GGT ATT GAA ATA TAT CAG GAT C
233             242         251             260         269
```

FIG. 11

```
                                                                                    -35
      AAG GTT GTT TNA CAT AAA ATG CCA ACC CNG NAA GCC TNT TNG NAA TAG ATC
       9               18              27              36              45
                      -10                  *                         rbs
                              start            start            Met Arg Cys Val Lys
CCG TTT ACA CTC ATG ATA TAA TAT AGT AGG GAT AGA TAA GTG ATG AGG TGT GTG AAG
         60              69              78              87              96             105
       start          start
Ser Met Ser Val Met Leu Asn Met UKN UKN Asn Lys Glu Ala Leu Ser Met Ala Glu
TCA ATG AGT GTA ATG CTA AAT ATG CNT NAA AAT AAA GAA GCA CTT AGT ATG GCC GAG
       117             126             135             144             153             162

Arg Ile Val Leu Asp Tyr Leu Ile Glu Asn Lys Thr Ile Leu Lys Asp Phe Ser Val
AGA ATT GTT TTA GAT TAC TTG ATA GAA AAT AAG ACA ATC CTG AAG GAT TTT AGT GTT
       174             183             192             201             210             219

Glu Lys Ile Ala Glu Ala Ala Tyr Thr Ser Pro Ala Ser Val Val Arg Met Cys Lys
GAA AAA ATT GCG GAA GCT GCT TAT ACA TCA CCC GCA TCT GTT GTT AGA ATG TGT AAG
       231             240             249             258             267             276

Lys Leu Gly Tyr Lys Gly Phe UKN Asp Phe Lys Ile Asp Phe Ile Leu Ala Asn Ser
AAA CTT GGA TAT AAA GGA TTC NAA GAT TTT AAA ATT GAT TTT ATT TTA GCA AAT TCT
       288             297             306             315             324             333

Lys Val Glu Ile Pro Glu Thr Ser Glu Tyr Thr Asp Ile Leu Ile Lys Asp Pro
AAA GTA GAA ATA CCA GAA ACA TCT GAG TAT ACG GAC ATT TTA ATT AAA GAT CCC
       345             354             363             372             381             390

Val UKN
GTC GNT TT
```

FIG. 12

```
    AGC TAG ATT AAG TAA NAT ATA GAA TAT GGT ATA ATT TAT TGA TGT ATA NCC
         10           19          28          37          46

CAA NAC AAT TTA TAT ATT TTT TCA ATC ATT NNA AAT ATA TAT TTA ATA NTG CTT TAT
         61          70          79          88          97         106

GGT ATT ATG ATA TGG TNN CNN AAA TAG AAC ATA AAA GGA GCA TGG TAA GTG GCT AAA
        118         127         136         145         154         163

CTC GAT CAA ACA AAA ACC CCA TTT TTT GAT AAA ATT AGA GCA TAT GGA GTC TCA GGA
        175         184         193         202         211         220

NCG NCG GCT TTA GAT GTT CCT GGT CAT AAA CTG GGT TCG ATT GAT AAT GAA TTT ACA
        232         241         250         259         268         277
   -10         *                                      -35
                                     start
                                     Met Asp UKN Asn Ala Pro Arg Gly Leu Asp
AGA TAT TTA GGA CAT AAC GTT TTT TCT ATG GAT NCA AAT GCA CCA AGA GGA CTT GAT
        289         298         307         316         325         334

Asn Leu Ser Lys Pro Lys Gly Val Ile Lys Glu Ala Gln Ala Leu Ala Ala Asp Ala
AAT TTA TCN AAA CCT AAA GGT GTC ATT AAG GAA GCA CAA GCA CTC GCA GCA GAT GCT
        346         355         364         373         382         391

Phe Gly Ala Asp Pro Val UKN
TTT GGT GCG GAT CCC GTC GNT TT
        403         412
```

MYCOPLASMA EXPRESSION SYSTEM

The invention was made with U.S. Government support under NIH contract R01 A124428. The Government may have certain rights in the invention

BACKGROUND OF THE INVENTION

This application is the U.S. national stage application of PCT/US93/07407 filed under 35 U.S.C. 371.

The class Mollicutes encompasses a group of organisms collectively known as "mycoplasmas," many of which are important human and agricultural pathogens. Despite this pathogenicity, little is known about the genetics of mycoplasmas. These organisms possess the smallest genome thought necessary for autonomous existence. Razin, *Microbiol. Rev.* 49: 419–55 (1985). Due to their simplicity, most mycoplasma species require complex media for growth because they lack many biosynthetic pathways. In view of such limitations, traditional genetic studies employing auxotrophic mutants have not been possible with these organisms.

Based on RNA homology, mycoplasmas are thought to be a product of degenerative evolution from Gram-positive organisms. Previous studies of 16S rRNA sequence homology have suggested that mycoplasmas are more closely related to Gram-positive organisms than Gram-negative organisms Weisburg et al., *J. Bacteriol.* 171: 6455–67 (1989). The differences in translational specificity that have been demonstrated between the Gram-negative and Gram-positive bacteria also appear to pertain to mycoplasmas as well. Hager & Rabinowitz, *The Molecular Biology of the Bacilli* 1–34 (Dubnau ed., Acad. Press 1985).

The simplicity of mycoplasmas offers advantages in the context of expression systems. For example, mycoplasmas lack lipopolysaccharide and other toxic wall constituents, which would allow for simplified purification of recombinantly produced proteins. Significant problems have existed, however, with using mycoplasmas as a recombinant expression system. Adequate stability of cloned genes has previously not been achieved. Moreover, previous attempts at creating mycoplasma-based expression systems have employed gram-negative promoters, which was necessitated by the unavailability and limited knowledge regarding mycoplasma promoters, generally. The transcriptional apparatus of gram-negative bacteria, however, is often unable to correctly recognize mycoplasma promoter sequences. For instance, it has been shown that, although the rRNA promoter of *Mycoplasma capricolum* is recognized by both *E. coli* and *M. capricolum* RNA polymerase, it is not properly recognized in *E. coli*. Gafny et al., *Nucl. Acids Res.* 16: 61–76 (1988). Thus, the recognition of the mycoplasma rRNA promoter is activated in *E. coli* under the stringent condition of amino acid starvation, which is opposite of the expected result. Additional problems exist with such use of gram-negative hosts. Signals may arise from transcription initiation at pseudo-promoter sites, which are caused by the high (A+T) content in the mycoplasma DNA of the fusion gene. Vollenweider et al., *Science* 205: 508–11 (1979). Notarnicola et al. have shown that *E. coli* initiated translation at internal sites in a *Mycoplasma hyorhinis* lipoprotein structural gene. *F. Biol.* 172: 2986–95 (1990). It has become apparent, therefore, that the use of *E. coli* as a cloning host to study promoter sequences from organisms with a high (A+T) content, such as mycoplasmas, should be limited.

The lack of genetic tools also has made the development of mycoplasma cloning systems difficult. Only two transposons, Tn916 and Tn4001, have been shown to be useful for studying mycoplasma genetics. Dybvig & Alderete, *Plasmid* 20: 33–41 (1988); Dybvig & Cassell, *Science* 235: 1392–94 (1987); Mahairas & Minion, *Plasmid* 21: 43–47 (1989). A number of broad host-range plasmids from Gram-positive bacteria have been examined as possible cloning vectors, but all have proven to be unstable. Dybvig, *Plasmid* 21: 155–60 (1989). Naturally occurring mycoplasma plasmids have also been examined as possible cloning vectors, but they have not been shown to maintain and express a cloned gene. Dybvig et al., *IOM Letts.* 1: 209–10 (1990); King & Dybvig, *Plasmid* 28: 86–91 (1992). A cloning system has been developed in spiroplasmas which uses a spiroplasma virus as a cloning vector, but the vector has a limited host range. Stamburski et al., *J. Bacterial.* 173: 2225–30 (1991); *Gene* 110: 133–34 (1992). Mahairas and Minion have developed a cloning system based on integration of cloned genes into mycoplasma chromosomes via homologous recombination. Mahairas, et al., *Gene* 93: 61–65 (1990); Mahairas & Minion, *J. Bacteriol.* 171: 1775–80 (1989). The stability and versatility of this system make it possible to incorporate DNA sequences into the host. This system, however, was not designed to express foreign DNA because it lacks proper regulatory elements.

The lack of expression vectors suitable for use in mycoplasmas also has handicapped the study and production of mycoplasma proteins. Recombinant production of mycoplasma proteins in *E. coli* is hampered by the unique codon usage of the mycoplasmas. For instance, many mycoplasma genre, such as Mycoplasma, Ureaplasma and Spiroplasma, read the conventional UGA stop codon as coding for tryptophan. Some mycoplasmas, such as *A. laidlawii*, appear not to, however. Accordingly, a conventional expression host, such as *E. coli*, ceases translation at UGA, which in a normal mycoplasma background would often encode tryptophan. Thus, translation of a mycoplasma polypeptide would be prematurely terminated in an *E. coli* recipient host. This problem can be avoided by employing a mycoplasma recipient host with a suitable vector for expressing the gene of interest.

SUMMARY OF THE INVENTION

It is an object of the present invention to system to identify mycoplasma regulatory regions containing regulatory sequences.

It is another object of the present invention to provide for the recombinant production of foreign proteins by mycoplasmas.

It is also an object of the present invention to provide mycoplasma regulatory sequences and regions containing these sequences for use in a recombinant expression system.

It still another object of the present invention to provide a plasmid comprising mycoplasma regulatory sequences and a site for inserting foreign DNA.

It is yet another object of the present invention to provide a plasmid where the mycoplasma regulatory sequences control the expression of the foreign DNA.

In achieving these objects, there has been provided, in accordance with one aspect of the present invention, an expression system employing mycoplasma regulatory sequences to control the expression of foreign DNA in host cells. Suitable host cells include the members of the class Mollicutes, such as Acholeplasma.

In accordance with another aspect of the present invention, there is provided a method for identifying mycoplasma regulatory elements via a gene fusion construct with a reporter gene, such as lacZ.

In accordance with still another aspect of the present invention, there is provided a plasmid comprising a mycoplasma promoter sequence and foreign DNA, which is transformed into an appropriate host in order to produce the protein encoded by the foreign DNA. The plasmid may further comprise mycoplasma DNA that is normally located upstream of a mycoplasma promoter in the native environment. The foreign DNA may include mycoplasma DNA. The mycoplasma regulatory sequences may be from Acholeplasma or other mycoplasma genre.

In accordance with yet another aspect of the present invention, the expression system can the include one or more complete mycoplasma regulatory region or one or more fragments thereof. Additionally, the expression vector of the present invention can include more than one mycoplasma regulatory sequence, or combinations of mycoplasma sequences or fragments thereof.

Other objects, features and advantages of the present invention will become apparent from the following description.

BRIEF DESCRIPTION OF THE FIGURES

Figure 1B:
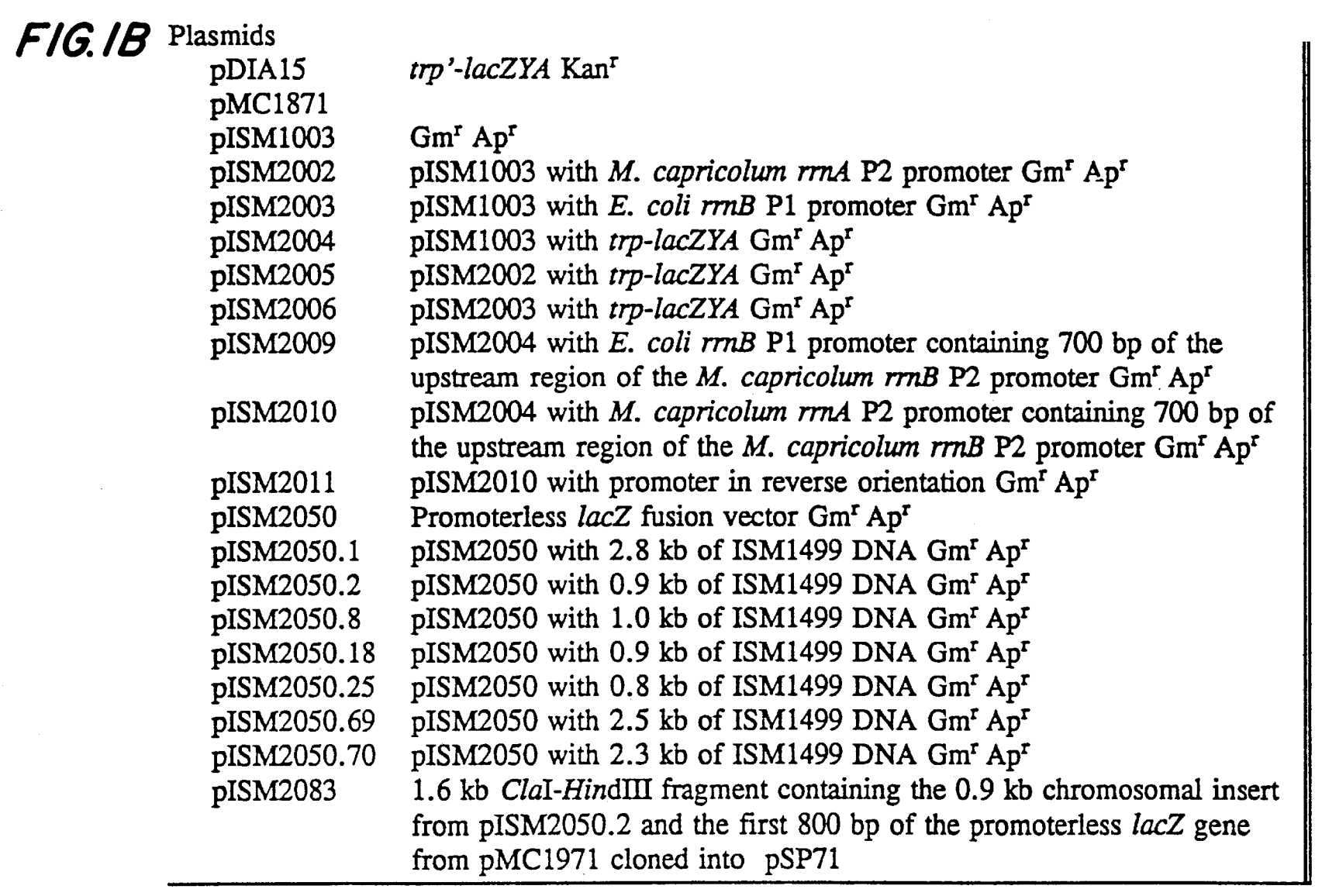

FIG. 1 is a chart of the major strains and plasmids employed to develop the present invention.

Genotypes/phenotypes of Acholeplasma transformants are defined by the nomenclature of "original strain::plasmid."

Figure 2:
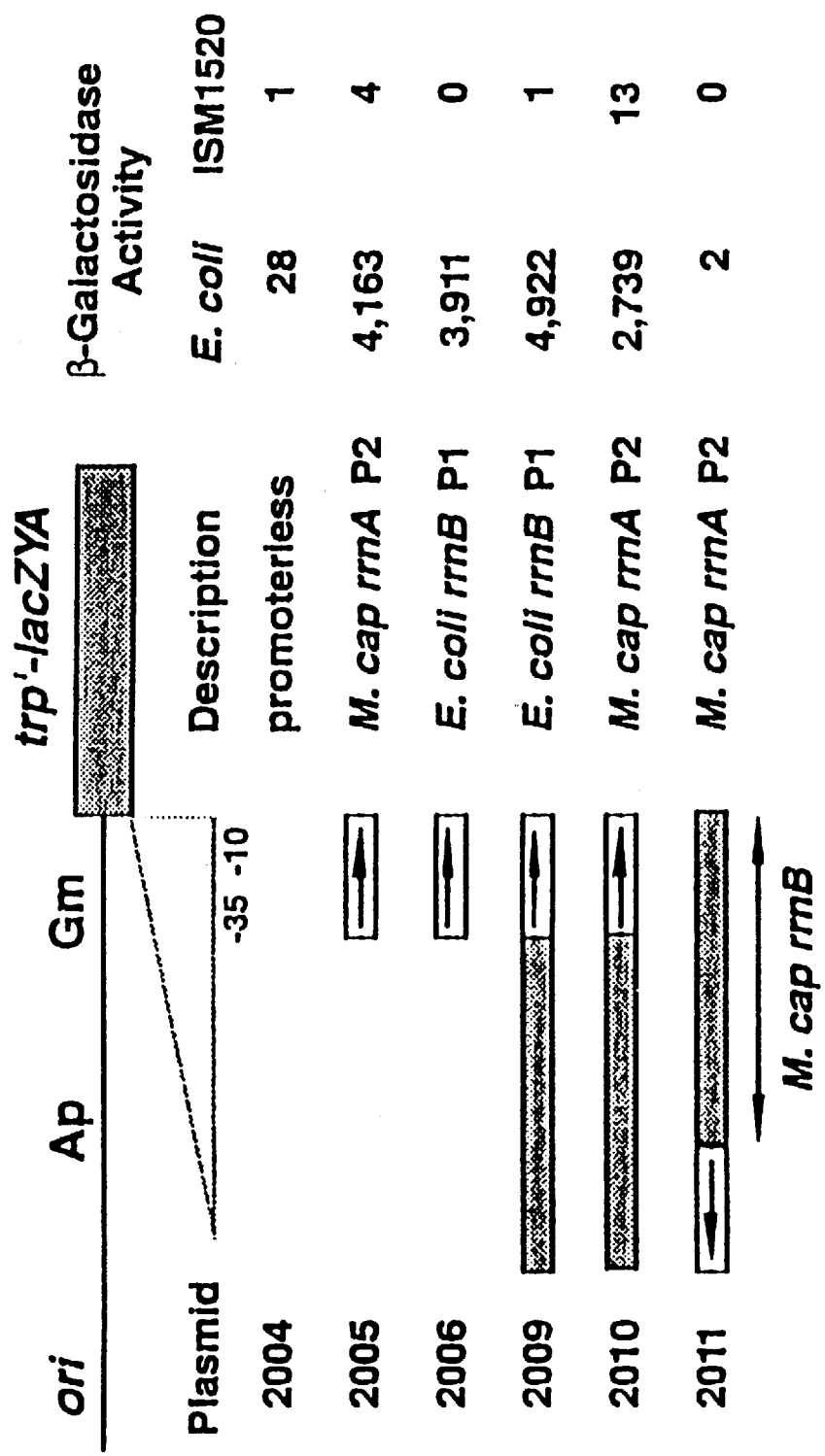
Figure 3:
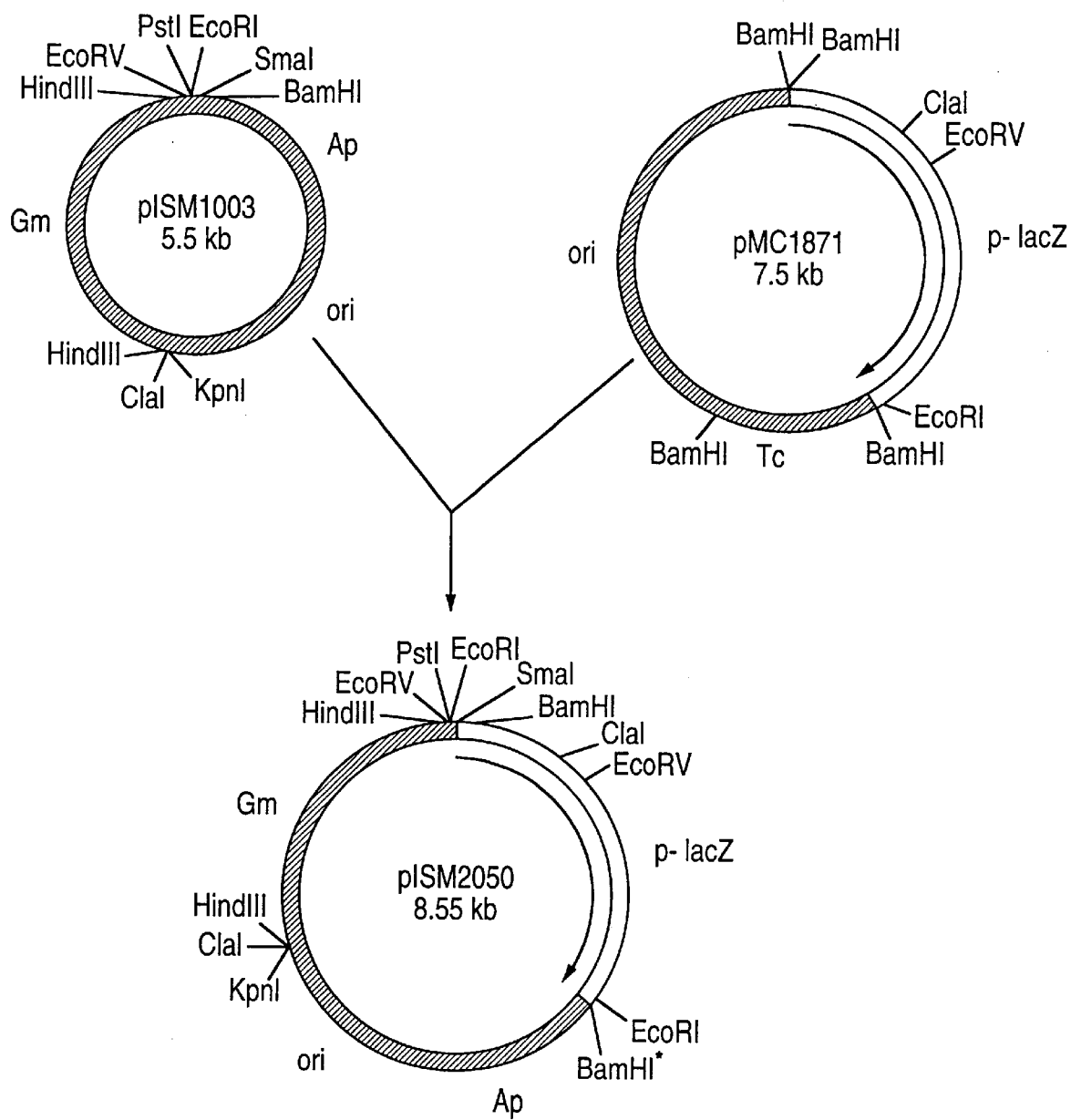

FIG. 2 depicts the construction of trp'-lacZYA fusion plasmids 2004, 2005, 2006, 2009, 2010 and 2011. Single headed arrows indicate the direction of transcription. The double headed arrow and the hatched bar denote the 700 bp region found upstream of the *M. capricolum* rrn P2 promoter. "M. cap." refers to *M. capricolum*; "Ap" refers to ampicillin resistance; "Gm" refers to gentamicin resistance; "ori" refers to origin of replication. This figure also sets forth β-galactosidase activity for *E. coli* CSH50 and Acholeplasma ISM1520 strains transformed with each plasmid.

FIG. 3 depicts the construction of the transcriptional fusion vector pISM2050. The vector was constructed by ligating a 3.1 kb BamHI DNA fragment containing the promoterless lacZ from plasmid pMC1871 into the BamHI site of plasmid pISM1003. The arrow indicates the direction of transcription of lacZ. The asterisk (*) indicates a BamHI site that was inactivated. "Ap" refers to ampicillin resistance; "Gm" refers to gentamicin resistance; "Tc" refers to tetracycline resistance; "p-lacZ" refers to promoterless lacZ ; ori refers to the origin of replication.

FIG. 4 depicts data from β-gal assays performed with seven of the lacZ fusion constructs introduced into ISM1520. CSH50 and χ289 served as controls.

FIG. 5 depicts the alignment and determination of putative −10 and −35 promoter regions (SEQ ID NOS:1–12) driving lacZ in plasmid pISM2050 derivatives based on similarity to a consensus *E. coli* promoter sequence. Bold letters indicate transcriptional start sites.

FIG. 6 depicts the sequence upstream (a region containing regulatory sequences (SEQ ID NOS:13–14) of the lacZ gene in fusion construct pISM2050.1. Additionally, the lacZ-chromosomal DNA fusion is shown in italics (GATC). The putative −35 and −10 promoter regions are underlined and the transcriptional start site is indicated by an (*). The potential ribosomal binding site (rbs) and translational start site (start) are also underlined. These designations are also employed in FIGS. 7–12.

FIG. 7 depicts the sequence (SEQ ID NOS:15–16) upstream of the lacZ gene in fusion construct pISM2050.2.

FIG. 8 depicts the sequence (SEQ ID NOS:17–18) upstream of the lacZ gene in fusion construct pISM2050.8.

FIG. 9 depicts the sequence (SEQ ID NOS:19–20) upstream of the lacZ gene in fusion construct pISM2050.18.

FIG. 10 depicts the sequence (SEQ ID NOS:21–22) upstream of the lacZ gene in fusion construct pISM2050.25.

FIG. 11 depicts the sequence (SEQ ID NOS:23–24) upstream of the lacZ gene in fusion construct pISM2050.69.

FIG. 12 depicts the sequence (SEQ ID NOS:25–26) upstream of the lacZ gene in fusion construct pISM2050.70. A potential ribosomal binding site ("rbs") was not found.

DETAILED DESCRIPTION OF PREFERRED EMBODIMENTS

A lack of specific information concerning mycoplasma regulatory sequences and regions containing these sequences heretofore has combined with an inability to readily detect or identify mycoplasma promoters and other regulatory sequences by means of cloning into *E. coli*. A system now has been developed, however, that allows for the reproducible identification of regions containing regulatory sequences of mycoplasmas. In particular, it has been discovered that a protein fusion construct, wherein a putative mycoplasma regulatory region is tested for an ability to drive expression of a reporter gene, lacZ, can be employed advantageously in a mycoplasma, such as an Acholeplasma host, thereby to confirm the existence of in actual regulatory sequence in the test region. The term "regulatory sequence" denotes any sequence that controls or affects the transcription of DNA into RNA or the translation of RNA into a protein. Exemplary of such regulatory sequences are promoters, ribosome binding sites, and translation start sites. A "regulatory region" contains regulatory sequences.

That the lacZ gene could fulfill such a reporter function in mycoplasma was not predictable in light of the uncertainty that generally surrounded heterologous expression in mycoplasma. Thus, there was little or no information previously available on whether mycoplasma tRNA concentration and availability could accommodate expression of an exogenous gene, on whether stability of foreign mRNA would be sufficient for such expression, or on whether an heterologous expression product, if obtained, would possess adequate stability in the mycoplasma host.

Other uncertainties existed as well. For instance, the conventional stop codon, UGA, is used in many mycoplasmas as a tryptophan-coding codon. Inamine et al., *J. Bacteriol.* 172: 504–06 (1990). It could not have been predicted whether this unique codon usage would interfere with the function of a reporter gene. In the context of the present invention, this consideration militates in favor of choosing a reporter gene that, like lacZ, lacks the UGA codon or is tolerant of the alternative UGA or other codon usage.

In view of the success of lacZ as a reporter gene in a mycoplasma, other commonly employed reporter genes might also be used in mycoplasmas. Problems may exist with employing other reporter genes in mycoplasma due, at least in part, to the alternative codon usage of mycoplasmas.

According to the present invention, an appropriate reporter gene with an upstream cloning site is useful for analysis of regulatory regions containing regulatory sequences of mycoplasmas. Use of an appropriate reporter gene can identify regulatory regions and assist in the analysis of defined mutations regulatory sequences. Accordingly, the present invention allows for the further identification and modification of mycoplasma regulatory sequences or regions containing these sequences.

Another aspect of the present invention relates to purified mycoplasma regulatory sequences or regions for use in an expression vector. The term "purified" in the context of this invention refers to a degree of purity greater than that found in nature, preferably a degree of purity that is sufficient for purposes of constructing an expression vector. The regulatory sequences or regions of the invention may be obtained by means such as isolation from natural sources or chemical synthesis. Purified fragments and derivatives of mycoplasma regulatory regions and sequences found in nature are also within the scope of this invention.

A further aspect of the present invention involves employing at least one mycoplasma regulatory sequence or region operably linked to foreign DNA in an expression vector. Because the regulatory sequence or region and foreign DNA are arranged in this manner, the regulatory sequence or region controls the expression of the foreign DNA when the vector is within a host, which preferably is a mycoplasma. Other appropriate hosts may be employed as well. The regulatory region, sequence, or fragments thereof may be combined when used in the expression system of the present invention. Cells transformed with these expression vectors are also within the scope of this invention.

In the context of this invention, the term "foreign DNA" includes any DNA that encodes the desired product. The foreign DNA can be isolated from natural sources, can be generated from RNA via reverse transcription or can be synthesized. Natural sources include any entity that possesses DNA or RNA, including mycoplasmas. For instance, the present invention includes the use of a mycoplasma host, such as Acholeplasma, transformed with a plasmid containing a mycoplasma regulatory sequence and a DNA sequence (that is, a foreign DNA) from a virus, bacterium, animal or plant. Additionally, the foreign DNA can be from a mycoplasma, even from an Acholeplasma. Preferably, the foreign DNA encodes a protein.

The recombinant production of mycoplasma proteins will allow for the identification of mycoplasma antigens useful for creating vaccines. Additionally, the production of antigenic mycoplasma proteins permits the development antibodies directed against mycoplasma antigens. Such antibodies would have diagnostic and therapeutic uses. The foreign non-mycoplasmal proteins produced by the present invention are also useful, especially in the context of vaccine production and development of antibodies.

The following examples are intended to further describe and discuss the construction and use of present invention. The invention, however, is not limited to the express terms of these examples.

EXAMPLE 1

Construction of lacZ Transcriptional Fusion Constructs with the *M. capricolum* rrnA P2 Promoter The use of *E. coli* lacZ as a reporter gene in mycoplasmas was evaluated by examining the ability of a known mycoplasma or *E. coli* promoter to generate β-galactosidase (β-gal) activity from a transcriptional fusion with the trp'-lacZYA operon. Gene fusions have proven to be powerful tools for studying prokaryotic transcriptional and translational control elements. Silhavy & Beckwith, *Microbiol. Rev.* 49: 398–418 (1985); Silhavy et al. EXPERIMENTS WITH GENE FUSIONS, COLD SPRING HARBOR (1984); Simons, et al., *Gene* 53: 85–96 (1987). This fusion employed *E. coli* translational start sites.

Plasmids pISM2004–2006 and pISM2009–2011 were constructed and transformed into *E. coli* CSH50 and Acholeplasma ISM1520. See FIG. 1. Acholeplasma strain designations ISM2004–2010 represent recombinants containing plasmid pISM2004-pSM2010, respectively. *E. coli* DH5α and χ289 were obtained from Bethesda Research Labs and R. Curtiss, respectively. Acholeplasma ISM1499 was a laboratory isolate. Acholeplasma ISM1520 was constructed by transformation of ISM1499 with the plasmid pISM1026 $Tc^r$. Plasmid pISM1026 $Tc^r$ is a derivative of cloning vector pSP64 (Promega), and contains the tetracycline resistance marker from TN916 and an approximately 5 kb fragment of Acholeplasma DNA (for insertion into the chromosome). Plasmid pDIA15 is disclosed in De Reuse et al., *FEMS Micro. Lett.* 37: 193–97 (1986). Plasmid pMC1871 is disclosed in Casadaban et al., *Meth. Enzymol.* 100:293–308 (1983). Plasmid pISM1003 is disclosed in Mahairas et al., *Gene* 93: 61–65 (1990). All other strains and plasmids were developed in conjunction with the present invention. The construction of the trp'-lacZYA plasmids are depicted in FIG. 2. First, the −35 and −10 regions of the *M. capricolum* rrnA P2 promoter or the −35 and −10 regions of the *E. coli* rrnB P1 promoter were cloned into the EcoRI and BamHI sites of plasmid pISM1003 (Mahairas & Minion, supra) to generate plasmids pISM2002 or pISM2003, respectively. Plasmids pISM2005 and pISM2006 were constructed by inserting the 7.1 kb BamHI fragment containing trp'-lacZYA from plasmid pDIA15 (De Reuse, et al., *FEMS Micro. Lett.* 37: 193–97 (1986)) downstream of the promoters in plasmids pISM2002 and pISM2003. See FIG. 2. Plasmids pISM2010 and pISM2009 are identical to plasmids pISM2005 and pISM2006, respectively, except that an additional 700 bp region upstream of the *M. capricolum* rrnB P2 promoter has been placed upstream of the promoters in the plasmids. Plasmid pISM2011 is identical to plasmid pISM2010 except that the *M. capricolum* promoter and rrnB P2 upstream sequences are in the reverse orientation. Acholeplasma cells were grown in PPLO broth (Difco Laboratories, Detroit, Mich.) supplemented with 15% gamma globulin-free horse serum (GIBCO Laboratories, Grand Island, N.Y.), 2.5% yeast extract, 0.5% glucose, 2.5 mg/ml of Cefobid (Pfizer, Inc., New York, N.Y.), 0.02% (wt/vol) DNA (Sigma Chemical Co., St. Louis, Mo.), 0.002% (wt/vol) phenol red, and (when required) 1% Noble agar (Difco). Selective levels of antibiotics for Acholeplasma ISM1499 were 2 mg/ml tetracycline (Sigma) and 15 mg/ml gentamicin (Sigma), and resistant cultures were maintained at 10 mg/ml tetracycline and 15 to 20 mg/ml gentamicin. *E. coli* cultures were grown in Luria broth containing 100 mg/ml ampicillin (Sigma) or 12.5 mg/ml tetracycline when appropriate.

The transformation of Acholeplasma was performed as described in Mahairas & Minion, *Plasmid* 21: 43–47 (1989). X-gal was dissolved in dimethyl sulfoxide, and was spread on the agar surface 1 to 2 hours prior to plating the transformation mixture. Transformation of *E. coli* was achieved by the method of Hanahan, *J. Mol. Biol.* 166: 557–80 (1983) or by electroporation using the BTX model 600 electroporator (Biotechnologies & Experimental Research, Inc., San Diego, Calif.), 1 mm gap, with settings of 0.81 kV, 50 μF, and 129 ohm, to generate a pulse length of 5 milliseconds.

Levels of β-gal activity of the transformants were measured and the results are set forth in FIG. 2. β-galactosidase assays were performed as described by Schleif & Wensink, PRACTICAL METHODS IN MOLECULAR BIOLOGY (Springer-Verlag 1981). First, 5 ml of an Acholeplasma culture was washed with PBS and the pellet was re-suspended in 2 ml of Z buffer (0.1M sodium phosphate, pH 7.0; 0.001M magnesium sulfate; 0.1M 2-mercaptoethanol). Fifty microliters of 0.1% SDS was added to 1 ml of the cell suspension and vortexed for 15 seconds. One hundred microliters of the lysed cell suspension was added to 1 ml of Z buffer and equilibrated to 37° C. Two hundred microliters of a 4 mg/ml o-nitrophenyl-β-D-galactopyranoside (Sigma) solution was added. The reaction was stopped by adding 0.5 ml of 1M sodium carbonate. The absorbance of the reaction was measured with a Spectronic 20 (Bausch & Lomb) at an absorbance of 420 nm. *E. coli* cultures were assayed in a similar manner except that 100 μl of a 1 ml culture was used and the cells were made permeable with 0.1% SDS and drops of chloroform. See Miller, EXPERIMENTS IN MOLECULAR BIOLOGY, COLD SPRING HARBOR LABORATORY, Cold Spring Harbor, N.Y. (1972). Fully induced *E. coli* strain χ289 was used as a positive control.

The generation of high levels of β-gal in *E. coli* using the *M. capricolum* rrnA P2 promoter showed that the *E. coli* RNA polymerase recognized *M. capricolum* promoter sequences. In contrast, the *E. coli* rrnB P1 promoter was not recognized by the Acholeplasma RNA polymerase as evidenced by the lack of mRNA produced. Although the −35 and −10 regions of these promoters were similar, the Acholeplasma RNA polymerase was more stringent, which supports previous studies using in vitro transcription assays. Gafny et al., *Nucl. Acids Res.* 16: 61–76 (1988).

The *M. capricolum* promoter was able to drive the expression of lacZ in both *E. coli* and Acholeplasma ISM1520, but the overall levels of β-gal activity in Acholeplasma were low in comparison to levels in *E. coli* Slightly higher levels of β-gal activity were generated in Acholeplasma with the additional 700 bp region from the *M. capricolum* rrnB P1 promoter region in plasmid pISM20110. This supported an earlier observation that the upstream region of the *M. capricolum* rrnB P2 promoter influences transcriptional levels. Josaitis et al., *Biochim. Biophys. Acta.* 1050: 307–11 (1990). The *M. capricolum* promoter in the reverse orientation with respect to lacZ (pISM2011) was not able to generate β-gal activity in either Acholeplasma or *E. coli.*

The low levels of β-gal activity in Acholeplasma were observed using the *M. capricolum* promoter in a trp'-lacZ operon fusion could be accounted for, in part, by the single copy insertion into the chromosome or by poor recognition of the *M. capricolum* promoter by the Acholeplasma RNA polymerase. A more likely explanation, however, is that the translation initiation region of the *E. coli* trp gene promoter was not efficiently recognized in Acholeplasma.

Slot blot analysis of RNA levels from Acholeplasma ISM1499, ISM1520, ISM2004, ISM2005, ISM2006, ISM2009, and ISM2010 were performed with either 16S rRNA, to standardize the assay, or a lacZ-specific probe. Counts per volume were detected by the PHOSPHORIMAGER (Molecular Dynamics, Sunnyvale, Calif.) and analyzed with the IMAGEQUANT program (Molecular Dynamics, Sunnyvale, Calif.). All blots with the 16S rRNA probe showed hybridization. The values obtained with the lacZ probe in counts per minute after subtracting background and adjusting for amounts of RNA loaded are set forth in parenthesis following the identification of the transformant: ISM1499 (0), ISM1520 (0), ISM2004 (40,652), ISM2005 (543,651), ISM2006 (0), ISM2009 (32,574), ISM2010 (329,117).

The trp'-lacZ TRNA transcript levels in ISM2005 and ISM2010 were relatively high despite the low levels of β-gal being produced. Both of these transformants contain the *M. capricolum* rrnA P2 promoter. Surprisingly, the *E. coil* consensus promoter (*E. coli* rrnB P1) alone in ISM2006 was not able to drive expression of lacZ in Acholeplasma despite close homology in the −10 and −35 sequences. See Gafny, et al., supra. Although the *E. coli* consensus promoter alone failed to produce significant levels, the addition of the 700 bp *M. capricolum* rrnB P1 upstream sequence (ISM2009) did yield detectable, but low levels of the lacZ transcript. Transcript levels of ISM2004 were detectable and were probably due to read through from adjacent genes, a common problem when using lacZ fusion vectors. Silhavy & Beckwith, supra; Simons, et al. supra.

EXAMPLE 2

The lacZ Protein Fusion Library Construction

Because only low levels of β-gal activity were generated from the transcriptional fusion system described above, a protein lacZ fusion construct was developed. Transcriptional and protein fusions are generally described in Casadaban et al., *Meth. Enzymol.* 100: 293–308 (1983). The protein fusion vector pISM2050 was constructed to increase β-gal activity by utilizing both mycoplasma transcriptional and translational sequences cloned upstream of the promoterless lacZ.

The construction of plasmid pISM2050 is illustrated in FIG. 3. The parent plasmid, pISM1003, was digested with BamHI and the 3.1 kb BamHI fragment of plasmid pMC1871 (Casadaban et al., supra) containing a promoterless lacZ gene was ligated into the site. In order to generate a unique site for cloning, the downstream BamHI site was removed by partial digestion with BamHI followed by a fill-in reaction with Klenow fragment of DNA polymerase I, ligation to circularize, and transformation into *E. coli*. Transformants were selected on ampicillin containing media, and the proper construct was confirmed by restriction enzyme analysis.

Plasmid pISM2050 was constructed with a gentamicin marker for selection in mycoplasmas, a promoterless lacZ reporter gene with unique upstream BamHI and SmaI restriction enzyme sites for cloning Sau3AI and blunt end fragments, respectively, and an ampicillin marker and origin of replication for amplification of DNA in *E. coli* prior to transformation into Acholeplasma. It should be noted, however, that when Sau3A1 fragments are ligated into BamHI sites, the BamHI site is often lost. The ampicillin gene and origin of replication also provided a region of homology to insert the plasmid into the Acholeplasma recipient strain ISM1520 via homologous recombination. See Mahairas & Minion, *J. Bacteriol.* 171: 1775–80 (1989); Mahairas et al., *Gene* 93: 61–66.

A library of cloned fragments was produced and screened for β-galactosidase activity in *E. coli* prior to introduction into Acholeplasma because of the large quantity of plasmid DNA (7 to 10 μg) required for transformation into mycoplasmas.

First, chromosomal DNA was prepared by washing the cells from a 500 ml culture with phosphate buffered saline (PBS, 10 mM sodium phosphate, 150 mM NaCl, pH 7.4) and re-suspending the pellet in 5 ml of NET buffer (0.1M Tris, 0.15M NaCl, and 0.08M EDTA, pH 7.5) containing 10 mg/ml Proteinase K. After 2 hours of incubation at 37° C., the cells were lysed with 1 ml of a detergent solution containing 1% sodium dodecyl sulfate (SDS), 1% Nonidet P-40, and 1% deoxycholate. After phenol extraction, the DNA was purified on a cesium chloride-ethidium bromide buoyant density gradient. DNA bands were collected, ethidium bromide extracted, and salt removed. Sambrook et al., MOLECULAR CLONING, A LABORATORY MANUAL, COLD SPRING HARBOR LABORATORY, Cold Spring Harbor, N.Y. (1989). The chromosomal DNA was partially digested with Sau3AI and fragments were separated by a sucrose gradient. Sambrook et al., loc. cit. One to six kilobase fragments were isolated and cloned into pISM2050 using standard recombinant DNA techniques as described below.

Acholeplasma ISM1499 Sau3AI-digested chromosomal DNA and BamHI-digested vector pISM2050 were ligated together, and the ligation mixtures were used to transform $E. coli$ DH5α. Approximately 20% of the $E. coli$ transformants demonstrated the blue phenotype. Restriction enzyme analysis of plasmid preparations from both blue and white colonies showed that all of the blue colonies contained plasmids with mycoplasmal chromosomal DNA inserts while only 20–30% of the white colonies had plasmids with inserts. As a result, only plasmids from blue colonies were used for further study. Plasmid DNA from five independent colonies were pooled together and used to transform Acholeplasma ISM1520. If a mycoplasma transformant from the plasmid pool demonstrated β-gal activity based on blue colony formation on X-gal-containing media, each plasmid DNA from that pool was then used to transform Acholeplasma ISM1520.

Interestingly, only 13 of the 140 (10.8%) recombinants that demonstrated promoter activity in $E. coli$ also showed activity in ISM1520. Possible explanations include: (1) pooled plasmid preparations in the initial transformation of ISM1520 were under-represented or did not successfully transform the promoter-containing constructs; or (2) the A+T rich mycoplasma DNA may have generated pseudo-promoter activity in $E. coli$. Identification of the event responsible for this result, however, is not needed for the practice of this invention.

Acholeplasma transformants containing lacZ fusion constructs displayed varying blue intensity on X-gal-containing media. β-gal assays were performed with seven of the lacZ fusion constructs that were introduced into ISM1520. The results set forth in FIG. 4 show that levels of β-gal production varied by 100-fold between the transformants containing the various lacZ fusion constructs. The varied production levels from cloned fragments indicate that gene regulation is occurring at the promoter and/or translational level in Acholeplasma. Immunoblot analysis and the intensity of blue color on X-gal containing media confirmed this conclusion.

Levels of the lacZ fusion transcripts were also measured for the ISM1520 strains harboring the lacZ fusion plasmids (FIG. 4). First, total RNA was prepared using RNA STAT-60 isolation reagent (Tel-Test "B", Inc., Friendswood, Tex.) according to manufacturer's instructions from a 4 ml overnight culture. Messenger RNA levels were measured by slot blot analysis using a Minifold II apparatus (Schleicher & Schuell, Keene, N. H.) and following the procedure described in Sambrook, et al. MOLECULAR CLONING, A LABORATORY MANUAL, COLD SPRING HARBOR (1989). Two micrograms of total RNA were placed into each slot and transferred to nitrocellulose (Schleicher & Schuell) and probed with a 1.4 kb fragment containing the 16S rRNA gene from ISM1499 or a 3.1 kb fragment containing the lacZ gene. The blot was exposed to x-ray film or was examined with a PHOSPHORIMAGER and analyzed with the INAGEQUANT program. Levels of the lacZ mRNA were adjusted by normalizing to the 16S rRNA levels to account for differences in amounts of RNA that may have been loaded in each slot for each strain. The results in FIG. 4 correlate with the β-gal assay results in that strains demonstrating higher transcript levels generally had higher levels of β-gal activity.

Protein concentration was measured by using the Bio-Rad protein assay (Bio-Rad, Richmond, Calif.) according to the manufacturer's directions. The number of colony forming units (CFU) per milligram of protein was determined by dividing the number of CFU/ml by mg/ml from the average of three cultures each measured in triplicate. The amount of β-gal enzyme required to give an OD=1.0 at an absorbance of 420 nm in one minute is $4.45 \times 10^{12}$ monomers. Towbin et al., $Proc. Nat'l Acad. Sci. U.S.A.$ 76: 4350–54 (1979). The levels of β-gal activity, therefore, was expressed as the number of monomers per CFU as shown below. Cultures were assayed in triplicate.

$$\text{Units of } \beta\text{-gal activity} = \frac{A_{420} \times 4.45 \times 10^{12} \text{ monomers}}{\text{time (min)} \times \text{mg protein} \times \text{CFU/mg}}$$

Immunoblot analysis was performed with several recombinant Acholeplasma strains to demonstrate the production of a β-gal fusion protein. Protein samples containing 25 μg protein from washed mycoplasmas were re-suspended in water and lysed with 0.01% (final concentration) SDS, then SDS-PAGE sample buffer (Laemmli, $Nature$ 227: 680–85 (1970) was added, and the samples were boiled for 5 minutes and then separated on a 7.5% polyacrylamide resolving gel. Following electrophoresis for 4 hours at 25 mAmp constant current, proteins were transferred to nitrocellulose following the procedure of Towbin, et al., $Proc. Nat'l Acad. Sci. USA$ 76: 4350–54 (1979). The blots were analyzed using a 1:3,000 dilution of a monoclonal antibody to β-gal (Promega) followed by goat anti-mouse antibody conjugated to alkaline phosphatase (Kirkegaard & Perry Laboratories, Inc., Gaithersburg, Md.) (1:1,000 dilution). The blot was developed by using the BCIP/NBT one component alkaline phosphatase substrate system (Kirkegaard & Perry Laboratories, Inc.). Acholeplasma ISM1520 strains with high levels of β-gal activity reacted more strongly with the anti-β-gal monoclonal antibody, which supports the results of the β-gal assay.

EXAMPLE 3

DNA Sequencing of Promoter-Containing DNA Fragments

The chromosomal DNA inserts adjacent to the lacZ gene in the pISM2050 derivatives were sequenced by using an oligonucleotide sequencing primer (SEQ ID NO:27). This primer (5'-GCTGGCGAAAGGGGGATGTGCTGCAAGGCG-3') is reverse and complimentary to the lacZ gene at approximately 50 nucleotides downstream of the lacZ-chromosomal DNA fusion point. Other sequencing primers, such as the T7, T3 and Mi3 forward and reverse primers, were also employed in the sequencing of chromosomal inserts. The SEQUENASE kit (United States Biochemical) is suitable for this sequencing.

The chromosomal inserts were sequenced by first subcloning the inserts into pSP71 (Promega Corp.) or isolating a ClaI fragment containing the insert, the junction site and a portion of lacZ from an agarose gel and purification with GeneClean. The fragments were removed from pISM2050 for sequence analysis because pISM2050 was derived from pKS (Stratagene), which also contains the portion of lacZ that is recognized by the sequencing primer.

EXAMPLE 4

Mapping of Acholeplasma IS1499 Promoters by Primer Extension

The transcriptional start sites for the promoters (SEQ ID NOS:1–12) driving the expression of lacZ in the fusion plasmids pISM2050.1, pISM2050.2, pISM2050.8, pISM2050.18, pISM2050.25, pISM2050.69, and pISM2050.70 were mapped by primer extension method of Ausebel et al., CURRENT PROTOCOLS IN MOLECULAR BIOLOGY (John Wiley & Sons 1989). See FIG. 5. Three microliters of the primer extension product were electrophoresed on an 8% sequencing gel. The primer extension products were compared to a sequencing ladder generated by using pISM2083 with the sequencing primer. The difference in the distance from the lacZ-chromosomal DNA fusion point to the base corresponding to the primer extension product was then mapped on a previously determined sequence map for each plasmid.

The transcriptional start sites and upstream region of the lacZ fusion transcripts for seven of the ISM2050 derivatives are shown in FIG. 5. The upstream regions were aligned to the putative sequences encompassing the −10 and −35 promoter regions. The regions were defined based on their similarity to the E. coli consensus promoter. Hawley and McClure, Nucl. Acids Res. 11: 2237–55 (1983). The spatial relationships between the transcriptional start and the −10 region as well as between the −10 region and the −35 region were similar to the E. coli consensus, promoter. The sequences upstream of the lacZ gene in pISM2050.1, pISM2050.2, pISM2050.8, pISM2050.18, pISM2050.25, pISM2050.69 and pISM2050.70 are set forth in FIGS. 6–12, (SEQ ID NOS:13–26) respectively. The potential ribosomal binding sites for each sequence were determined by aligning the sequence with the last 15 bp at the 3' end of the 16S rRNA gene of A. laidlawii.

A consensus promoter sequence for the seven pISM2050 fusion derivatives in the −10 and −35 regions were TATaW and TtcAtn, respectively. Upper case letters denote that at least 5 of the 7 pISM2050 derivatives contain the base. Lower case letters denote that at least 3 of the 7 pISM2050 derivatives contain the base in the designated position. "W" denotes A or T, and "n" denotes any base. See FIG. 5. The average number of bases that align between the ISM1499 promoter regions and the E. coli consensus promoter regions are 4.4 bp for the −10 region and 3 bp for the −35 region. The 3 bp conservation at the −35 region is about 1 bp less than the 3.9 bp observed with the E. coli and phage promoters. See FIG. 5. The observation that the −10 region was more like the E. coli consensus promoter than the −35 region is consistent with previous reports examining the putative mycoplasma promoter regions. Christiansen, Microbiol. Sci. 4: 168–72, 292–95 (1987); Muto et al., MOLECULAR BIOLOGY AND PATHOGENESIS at 331–48 (Maniloff et al. Eds., Amer. Soc. Micro. 1992); Inamine, et al., Gene 73: 175–83 (1988).

The result that the Acholeplasma promoters were similar to the E. coli consensus promoter is not unexpected because the lacZ fusion constructs were initially screened in E. coli based on their ability to give the Lac+ phenotype. The primer extension studies showed that the Acholeplasma ISM1499 chromosomal sequences adjacent to lacZ in the plasmid derivatives of pISM2050 contained the promoters that were driving the expression of lacZ. The sequences upstream of the transcriptional start sites were aligned (FIG. 5). Defining a mycoplasma promoter by its similarity to the E. coli consensus promoter could potentially be misleading, however, because mycoplasma DNA, like E. coli promoters, are A+T rich. Therefore, in order to precisely identify a mycoplasma promoter in a mycoplasma regulatory region, it is important to correlated sequence data with promoter mapping studies. Exact identification of the mycoplasma promoter, however, is not needed for the practice of this invention.

FIGS. 6–12 set forth sequence data from several mycoplasma regulatory regions, which contain regulatory sequences. These regulatory regions, or fragments of these regions, can be used to construct an expression vector suitable for expressing foreign DNA sequences (typically genes) in mycoplasmas, such as Acholeplasma. An expression vector within this invention could include the entirety of one of the mycoplasma regulatory regions identified in FIGS. 6–12, or one or more fragments thereof. Additionally, the expression vector of the present invention can include more than one mycoplasma regulatory region or sequence. Moreover, the expression system can include combinations of mycoplasma regions, sequences one fragments thereof.

EXAMPLE 5

Construction of a Mycoplasma Expression Vector

The expression vector pISM303 was constructed as follows. Primers PK101910 (SEQ ID NO:28)—5' GACG @gTTAAATACTAA 3' and PK101912 (SEQ ID NO:29)— 5' CGTAAGCTTCCTCCAACAACAAAAACCTTGA 3' were constructed to obtain the mycoplasma regulatory region contained in pISM2050.2. Primer PK101910 creates a BamHI site and primer PK101912 creates a HindIII site, both of which are underlined in the above sequences. In a polymerase chain reaction with plasmid pISM2050.2 (FIG. 7), the primers yielded a 260 base pair fragment that contained the putative −35 and −10 transcriptional start sites, a ribosomal binding site, an ATG translational start site and 24 codons of a mycoplasma structural gene. During the PCR reaction the upstream BamHI site that had been lost during pISM2050.2 construction was recreated for cloning purposes. The 260 bp fragment was digested with HindIII and BamHI and cloned into the general cloning vector pKS II(−) (Stratagene) to create plasmid pISM303. Cloning vector pKSII(−) is appropriate because it includes a multiple cloning site and an origin of replication. Other cloning vectors, however, are suitable for use in the present invention.

To test pISM303, a promoterless tetM gene was constructed by PCR and inserted into the unique BamHI site of pISM303. Plasmids with the proper tetM orientation confirmed by restriction analysis were transformed into E. coli or Acholeplasma ISM1503. Acholeplasma ISM1503 was obtained by transforming strain ISM1499 with pISM1007. This integrative plasmid is a pKS derivative that encoders the gentamicin resistance marker from TN4001. See Mahairais & Minion, J. Bacteriol. 171:1775–80 (1989). Other bacterial and mycoplasmal recipient strains are suitable for use with the present invention as well.

Plasmid pISM303 integrates into the genome of Acholeplasma ISM1503 by homologous recombination between the common ampicillin resistance marker sequences. Other regions can be employed as well, as long as the expression vector and the recipient strain possess a homologous region.

E. coli and Acholeplasma transformants were identified by tetracycline resistance arising from expression of tetM controlled by the mycoplasmal regulatory sequence in pISM303, thereby further demonstrating the usefulness of the present invention.

It should be understood that the description, examples and figures set forth above are given by way of illustration and explanation only, because various changes and modifications within the spirit and scope of the invention will become apparent to those skilled in the art in view of the description, examples and figures.

---

What is claimed is:

1. A method for identifying mycoplasma regulatory sequences, comprising the steps of:
   obtaining a gene fusion construct comprising a reporter gene,
   inserting mycoplasma DNA into said protein fusion construct upstream of the reporter gene, and
   determining whether the reporter gene is expressed in a mycoplasma host.

2. A method for identifying mycoplasma regulatory sequences according to claim 1, wherein said reporter gene is lacZ.

3. A purified mycoplasma regulatory region comprising at least one mycoplasma regulatory sequence, wherein the regulatory sequence is selected from the group consisting of regulatory sequences contained in FIG. 6 (SEQ ID NO:13), FIG. 7 (SEQ ID NO:15), FIG. 8 (SEQ ID NO:17), FIG. 9 (SEQ ID NO:19), FIG. 10 (SEQ ID NO:21), FIG. 11 (SEQ ID NO:23), and FIG. 12 (SEQ ID NO:25).

4. A purified mycoplasma regulatory sequence, wherein the sequence is selected from the group consisting of SEQ ID NO:1, SEQ ID NO.3, SEQ ID NO:5, SEQ ID NO:7, SEQ ID NO:9, SEQ ID NO:10, and SEQ ID NO:12.

5. A purified mycoplasma regulatory sequence according to claim 4, wherein the sequence is in an expression vector.

6. A purified mycoplasma regulatory sequence according to claim 5, wherein the expression vector is in a host cell.

7. A purified mycoplasma regulatory sequence according to claim 6, wherein the host cell is a member of the class Mollicutes.

8. A purified mycoplasma regulatory sequence according to claim 7, wherein the host cell is a member of the genus Acholeplasma.

9. An expression vector comprising (a) a mycoplasma regulatory region having at least one mycoplasma regulatory sequence and (b) a site for inserting foreign DNA downstream of the regulatory sequence, wherein the mycoplasma regulatory sequence is selected from the group consisting of regulatory sequences contained in FIG. 6 (SEQ ID NO:13), FIG. 7 (SEQ ID NO:15), FIG. 8 (SEQ ID NO:17), FIG. 9 (SEQ ID NO:19), FIG. 10 (SEQ ID NO:21), FIG. 11 (SEQ ID NO:23), and FIG. 12 (SEQ ID NO:25).

10. An expression vector according to claim 9, further comprising a foreign DNA inserted into the site.

11. An expression vector according to claim 10, wherein the vector is within a host cell.

12. An expression vector according to claim 11, wherein the host cell is a member of the class Mollicutes.

13. An expression vector according to claim 12, wherein the host cell is a member of the genus Acholeplasma.

14. A host cell for expressing a protein, wherein the host cell comprises an expression vector comprising (a) a mycoplasma regulatory region having at least one mycoplasma regulatory sequence and (b) and a foreign DNA encoding the protein downstream of the regulatory sequence, wherein the mycoplasma regulatory sequence is selected from the group consisting of regulatory sequences contained in FIG. 6 (SEQ ID NO:13), FIG. 7 (SEQ ID NO:15), FIG. 8 (SEQ ID NO:17), FIG. 9 (SEQ ID NO:19), FIG. 10 (SEQ ID NO:21), FIG. 11 (SEQ ID NO:23), and FIG. 12 (SEQ ID NO:25).

15. A host cell according to claim 14, further comprising a foreign DNA inserted into the site.

16. A host cell according to claim 14, wherein the host cell is a member of the class Mollicutes.

17. A host cell according to claim 16, wherein the host cell is a member of the genus Acholeplasma.

18. A method of producing a protein, comprising:
   providing a host cell comprising an expression vector comprising (a) a mycoplasma regulatory region having at least one mycoplasma regulatory sequence and (b) a foreign DNA encoding the protein downstream of the regulatory sequence, wherein the mycoplasma regulatory sequence is selected from the group consisting of regulatory sequences contained in FIG. 6 (SEQ ID NO:13), FIG. 7 (SEQ ID NO:15), FIG. 8 (SEQ ID NO:17), FIG. 9 (SEQ ID NO:19), FIG. 10 (SEQ ID NO:21), FIG. 11 (SEQ ID NO:23), and FIG. 12 (SEQ ID NO:25); and
   growing the host cell under conditions to express the protein.

19. A method according to claim 18, wherein the host cell a member of the class Mollicutes.

20. A method according to claim 19, wherein the protein is to be used as a vaccine.

21. A method according to claim 20, wherein the foreign DNA is from a mycoplasma.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TCACTGCACC TGAAGAACTA CATAAATATA AACTTGAAGA A        41

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CAAGAATTGC TAATG        15

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TATCTTCCTT TAATTACTAT TATATAGTAT AATATAAAAA GT        42

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TTGGAGTGAT AAGATG        16

( 2 ) INFORMATION FOR SEQ ID NO:5:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTACGCTACA ATCTAAAACC CAAATTGGTC AAGTACATGC TGAA 44

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TTAGTGCACA AACACTGATG 20

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AGAATTCATG CTTAAATCAC CTTTATATTT AAATAATCCA TCAGT 45

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CAAAGGTTTA GAACAAATG 19

( 2 ) INFORMATION FOR SEQ ID NO:9:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATTGTTGATG TATTCATACA TGATATAATA TATACGCGAA AGTGTTGAGG AATACAAATG 60

( 2 ) INFORMATION FOR SEQ ID NO:10:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TAGTAATAGA TCCCGTTTAC ACTCATGATA TAATATAGTA GGGG 44

( 2 ) INFORMATION FOR SEQ ID NO:11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TGTGAAGTCA ATG                                                                                          13

( 2 ) INFORMATION FOR SEQ ID NO:12:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGGTTCGATT GATAATGAAT TTACAAGATA TTTAGGACAT AACGTTTTTT CTATG            55

( 2 ) INFORMATION FOR SEQ ID NO:13:

( i ) SEQUENCE CHARACTERISTICS:
        ( A ) LENGTH: 443 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 427..441

( i x ) FEATURE:
        ( A ) NAME/KEY: mat_peptide
        ( B ) LOCATION: 427..441

( x i ) SEQUENCE DESCRIPTION: SEQ ID NO:13:

CCAGTGGNCC TCATNCTGAG TATGAAAAAC TCCCAAATCT TGGTCAAGNA GGTACNTTAT        60

TATTAGTATC TGACTCTACC AATNCTGAAC AAGAAGGTTT GANTCAATCT GAATCTAAAG      120

TTGGTAAATC CATTAACGAA CTCTTCACAA GAATTCCAGG ACGTATTATT ATTGCAACCT      180

TTGCATCCAA CTTGTATCGA ATTCAACAAA TTATTGAAGC ATCTGAATTA ACAGGTAGAA      240

AAGTTGCTGT TTTTGGACGT TCTATGGAAC GTGCTATTGA GGCTGGACAA CAATCAGGCT      300

ATATTAAACC TAGAAAAGGT ACATTCACTG CACCTGAAGA ACTACATAAA TATAAACTTG      360

AAGAAACTTG TATTTGGTT ACTGGTTCCC AAGGTGAACC ACTTGCAGCA TTATCAAGAA       420

TTGCTA ATG GAT CCC GTC GTT TT                                         443
      Met Asp Pro Val Val
       1               5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

Met Asp Pro Val Val
 1               5

( 2 ) INFORMATION FOR SEQ ID NO:15:

( i ) SEQUENCE CHARACTERISTICS:
        ( A ) LENGTH: 374 base pairs
        ( B ) TYPE: nucleic acid
        ( C ) STRANDEDNESS: single
        ( D ) TOPOLOGY: linear ( i x ) FEATURE:
        ( A ) NAME/KEY: mat_peptide
        ( B ) LOCATION: 289..372

( i x ) FEATURE:
   ( A ) NAME/KEY: CDS
   ( B ) LOCATION: 289..372

( x i ) SEQUENCE DESCRIPTION: SEQ ID NO:15:

```
GTCTTGGATG  AAGTCTTAAA  GCACCACCGA  TACTCATACC  TGAATTAATC  CCATATTTTC     60

TTGCTTTATA  ACTTGCAGTT  GATATAACAC  CTCTTGCATA  TGAGGATTGT  CCTCCAACAA    120

CAAAAACCTT  GTTTTTAAGG  TAAGGTTCTT  TAAGTATCGC  GCATGTTGCA  AAGAACGCAT    180

TTAAGTCGAT  ATGAAAAATA  ATTTTAGCCG  TTTTTTTCAT  CATTATCTTC  CTTTAATTAC    240

TATTATATAG  TATAATATAA  AAAGTATAAG  ATTATTTGGA  GTGATAAG ATG GCA CAA      297
                                                         Met Ala Gln
                                                          1
```

```
AAT  AAG  ACA  GCA  ACA  AAA  GAA  AAG  GCA  GTA  AAG  CCT  GCT  AAA  AAA  GAA     345
Asn  Lys  Thr  Ala  Thr  Lys  Glu  Lys  Ala  Val  Lys  Pro  Ala  Lys  Lys  Glu
          5                        10                       15

TCT  TTA  GTA  TTT  AAA  GAT  CCC  GTC  GTT  TT                                    374
Ser  Leu  Val  Phe  Lys  Asp  Pro  Val  Val
20                        25
```

( 2 ) INFORMATION FOR SEQ ID NO:16:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: protein ( x i ) SEQUENCE DESCRIPTION: SEQ ID NO:16:

```
Met  Ala  Gln  Asn  Lys  Thr  Ala  Thr  Lys  Glu  Lys  Ala  Val  Lys  Pro  Ala
 1                    5                        10                       15

Lys  Lys  Glu  Ser  Leu  Val  Phe  Lys  Asp  Pro  Val  Val
               20                        25
```

( 2 ) INFORMATION FOR SEQ ID NO:17:

( i ) SEQUENCE CHARACTERISTICS:
    ( A ) LENGTH: 359 base pairs
    ( B ) TYPE: nucleic acid
    ( C ) STRANDEDNESS: single
    ( D ) TOPOLOGY: linear ( i x ) FEATURE:
    ( A ) NAME/KEY: mat_peptide
    ( B ) LOCATION: 337..357

( i x ) FEATURE:
    ( A ) NAME/KEY: CDS
    ( B ) LOCATION: 337..357

( x i ) SEQUENCE DESCRIPTION: SEQ ID NO:17:

```
CGAGTAAGTA  ACATTATTAA  CTATGTAACA  ACATCCTTAG  CAATTGTCAA  AGATAATGAT     60

TTCGCAATTG  TAGAATCATT  TAAACGAGAG  GTTATGTAAT  TTATCCAAAC  ATTTAAAGGC    120

ATTGNGGTCT  CCAGTGGAGT  TGCAATTCCA  AAAATACATC  ACTTAGCTGA  AACCACTCAG    180

ATGAGCTTAA  AAAAGTTTTC  AACGGATAAA  AATGTTGAAC  TTAATCGTTT  TAATGAAACG    240

ATTAAAGAAG  CTGTTTCTCA  ATTAGAATTA  CTTACGCTAC  AATCTAAAAC  CGAAATTGGT    300

CAAGTACATG  CTGAAATCTT  TAGTGCACAA  ACACTG ATG  TTA  AAA  GAT  CCC  GTC    354
                                           Met  Leu  Lys  Asp  Pro  Val
                                            1                        5

GTT  TT                                                                    359
Val
```

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Leu  Lys  Asp  Pro  Val  Val
 1                 5
```

( 2 ) INFORMATION FOR SEQ ID NO:19:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i x ) FEATURE:
        ( A ) NAME/KEY: mat_peptide
        ( B ) LOCATION: 355..393

( i x ) FEATURE:
        ( A ) NAME/KEY: CDS
        ( B ) LOCATION: 355..393

( x i ) SEQUENCE DESCRIPTION: SEQ ID NO:19:

```
AGTAGNATCA  CTCAACCAAT  AATNNTTGAA  GTCTCTNAAN  CCAGTTTTGA  ATATGTGAAT      60

ACNCNANACA  TTATNNAAGA  TGCTAATATT  CCAAGAGGGT  CTTTTTACCA  GTACTTTGAA     120

GATAAGNCGG  ATATGTATGA  ATATATCATG  GATTATATTA  GTTCAATAAA  AAGATATTAT     180

TTTAAAAGTA  TATTTGAAGC  AGTGAATCTG  AATTTTATAG  AGCGAATAGA  GGCAATTTAT     240

TTAGCGGGTG  TAAAATTTAA  GTCCGAGAAC  CCTGATTTTG  TAAGAGCAGG  AGAATTCATG     300

CTTAAATCAC  CTTTATATTT  AAATAATCCA  TCAGTANCCA  AAGGTTTAGA  ACAA ATG       357
                                                                  Met
                                                                   1

ATT  TCA  ATC  TAC  GAG  TCT  TGG  ATT  ATC  AAT  GAT  CCC                 393
Ile  Ser  Ile  Tyr  Glu  Ser  Trp  Ile  Ile  Asn  Asp  Pro
             5                        10
```

( 2 ) INFORMATION FOR SEQ ID NO:20:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met  Ile  Ser  Ile  Tyr  Glu  Ser  Trp  Ile  Ile  Asn  Asp  Pro
 1                 5                        10
```

( 2 ) INFORMATION FOR SEQ ID NO:21:

( i ) SEQUENCE CHARACTERISTICS:
        ( A ) LENGTH: 268 base pairs
        ( B ) TYPE: nucleic acid
        ( C ) STRANDEDNESS: single
        ( D ) TOPOLOGY: linear ( i x ) FEATURE:
        ( A ) NAME/KEY: mat_peptide
        ( B ) LOCATION: 100..267

( i x ) FEATURE:
    ( A ) NAME/KEY: CDS
    ( B ) LOCATION: 100..267

( x i ) SEQUENCE DESCRIPTION: SEQ ID NO:21:

```
AAGTTTTTTT ATCACTTTGA CTTTGAACTC TTCTGCTTGT CTATTTCATT GATGTATTCA           60

TACATGATAT AATATATACG CGAAAGTTGA GGAATACAA ATG AAA TAC TTA GTT             114
                                          Met Lys Tyr Leu Val
                                            1               5

GGC ACT TAT ACT AAA AAT CTA TCC GAA GGT ATT TAC TTA GTT GAT GAG            162
Gly Thr Tyr Thr Lys Asn Leu Ser Glu Gly Ile Tyr Leu Val Asp Glu
                 10                  15                  20

GAT AAA GTC TCT TTA CAT ATG AGA TTA TTT AAT CCA ACT TAT TTT ACT            210
Asp Lys Val Ser Leu His Met Arg Leu Phe Asn Pro Thr Tyr Phe Thr
             25                  30                  35

TTA CAA GAA GGT CAT TTA TTT ACA ATT GCT AGA GGA GGT ATT GAA ATA            258
Leu Gln Glu Gly His Leu Phe Thr Ile Ala Arg Gly Gly Ile Glu Ile
         40                  45                  50

TAT CAG GAT C                                                              268
Tyr Gln Asp
 55
```

( 2 ) INFORMATION FOR SEQ ID NO:22:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met Lys Tyr Leu Val Gly Thr Tyr Thr Lys Asn Leu Ser Glu Gly Ile
 1               5                  10                  15

Tyr Leu Val Asp Glu Asp Lys Val Ser Leu His Met Arg Leu Phe Asn
             20                  25                  30

Pro Thr Tyr Phe Thr Leu Gln Glu Gly His Leu Phe Thr Ile Ala Arg
         35                  40                  45

Gly Gly Ile Glu Ile Tyr Gln Asp
 50                  55
```

( 2 ) INFORMATION FOR SEQ ID NO:23:

( i ) SEQUENCE CHARACTERISTICS:
        ( A ) LENGTH: 401 base pairs
        ( B ) TYPE: nucleic acid
        ( C ) STRANDEDNESS: single
        ( D ) TOPOLOGY: linear ( i x ) FEATURE:
        ( A ) NAME/KEY: mat_peptide
        ( B ) LOCATION: 94..399

( i x ) FEATURE:
        ( A ) NAME/KEY: CDS
        ( B ) LOCATION: 94..399

( x i ) SEQUENCE DESCRIPTION: SEQ ID NO:23:

```
AAGGTTGTTT NACATAAAAT GCCAACCCNG NAAGCCTNTT NGNAATAGAT CCCGTTTACA           60

CTCATGATAT AATATAGTAG GGATAGATAA GTG ATG AGG TGT GTG AAG TCA ATG          114
                                    Met Arg Cys Val Lys Ser Met
                                      1               5

AGT GTA ATG CTA AAT ATG CNT NAA AAT AAA GAA GCA CTT AGT ATG GCC            162
Ser Val Met Leu Asn Met Xaa Xaa Asn Lys Glu Ala Leu Ser Met Ala
```

|  |  |  |  |  | 10 |  |  |  |  | 15 |  |  |  |  | 20 |  |
|---|---|---|---|---|---|---|---|---|---|---|---|---|---|---|---|---|
| GAG | AGA | ATT | GTT | TTA | GAT | TAC | TTG | ATA | GAA | AAT | AAG | ACA | ATC | CTG | AAG | 210 |
| Glu | Arg | Ile | Val | Leu | Asp | Tyr | Leu | Ile | Glu | Asn | Lys | Thr | Ile | Leu | Lys | |
|  | 25 |  |  |  | 30 |  |  |  |  | 35 |  |  |  |  |  | |
| GAT | TTT | AGT | GTT | GAA | AAA | ATT | GCG | GAA | GCT | GCT | TAT | ACA | TCA | CCC | GCA | 258 |
| Asp | Phe | Ser | Val | Glu | Lys | Ile | Ala | Glu | Ala | Ala | Tyr | Thr | Ser | Pro | Ala | |
| 40 |  |  |  |  | 45 |  |  |  |  | 50 |  |  |  |  | 55 | |
| TCT | GTT | GTT | AGA | ATG | TGT | AAG | AAA | CTT | GGA | TAT | AAA | GGA | TTC | NAA | GAT | 306 |
| Ser | Val | Val | Arg | Met | Cys | Lys | Lys | Leu | Gly | Tyr | Lys | Gly | Phe | Xaa | Asp | |
|  |  |  |  | 60 |  |  |  |  | 65 |  |  |  |  | 70 |  | |
| TTT | AAA | ATT | GAT | TTT | ATT | TTA | GCA | AAT | TCT | AAA | GTA | GAA | ATA | CCA | GAA | 354 |
| Phe | Lys | Ile | Asp | Phe | Ile | Leu | Ala | Asn | Ser | Lys | Val | Glu | Ile | Pro | Glu | |
|  |  |  | 75 |  |  |  |  | 80 |  |  |  |  | 85 |  |  | |
| ACA | TCT | GAG | TAT | ACG | GAC | ATT | ATT | TTA | ATT | AAA | GAT | CCC | GTC | GNT |  | 399 |
| Thr | Ser | Glu | Tyr | Thr | Asp | Ile | Ile | Leu | Ile | Lys | Asp | Pro | Val | Xaa |  | |
|  |  | 90 |  |  |  |  | 95 |  |  |  |  | 100 |  |  |  | |
| TT |  |  |  |  |  |  |  |  |  |  |  |  |  |  |  | 401 |

(2) INFORMATION FOR SEQ ID NO:24:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:24:

| Met | Arg | Cys | Val | Lys | Ser | Met | Ser | Val | Met | Leu | Asn | Met | Xaa | Xaa | Asn |
|---|---|---|---|---|---|---|---|---|---|---|---|---|---|---|---|
| 1 |  |  |  | 5 |  |  |  |  | 10 |  |  |  |  | 15 |  |
| Lys | Glu | Ala | Leu | Ser | Met | Ala | Glu | Arg | Ile | Val | Leu | Asp | Tyr | Leu | Ile |
|  |  |  | 20 |  |  |  |  | 25 |  |  |  |  | 30 |  |  |
| Glu | Asn | Lys | Thr | Ile | Leu | Lys | Asp | Phe | Ser | Val | Glu | Lys | Ile | Ala | Glu |
|  |  | 35 |  |  |  |  | 40 |  |  |  |  | 45 |  |  |  |
| Ala | Ala | Tyr | Thr | Ser | Pro | Ala | Ser | Val | Val | Arg | Met | Cys | Lys | Lys | Leu |
|  | 50 |  |  |  |  | 55 |  |  |  |  | 60 |  |  |  |  |
| Gly | Tyr | Lys | Gly | Phe | Xaa | Asp | Phe | Lys | Ile | Asp | Phe | Ile | Leu | Ala | Asn |
| 65 |  |  |  |  | 70 |  |  |  |  | 75 |  |  |  |  | 80 |
| Ser | Lys | Val | Glu | Ile | Pro | Glu | Thr | Ser | Glu | Tyr | Thr | Asp | Ile | Ile | Leu |
|  |  |  |  | 85 |  |  |  |  | 90 |  |  |  |  | 95 |  |
| Ile | Lys | Asp | Pro | Val | Xaa |  |  |  |  |  |  |  |  |  |  |
|  |  |  | 100 |  |  |  |  |  |  |  |  |  |  |  |  |

(2) INFORMATION FOR SEQ ID NO:25:

(i) SEQUENCE CHARACTERISTICS:
        (A) LENGTH: 416 base pairs
        (B) TYPE: nucleic acid
        (C) STRANDEDNESS: single
        (D) TOPOLOGY: linear (ix) FEATURE:
        (A) NAME/KEY: mat_peptide
        (B) LOCATION: 307..414

(ix) FEATURE:
        (A) NAME/KEY: CDS
        (B) LOCATION: 307..414

(xi) SEQUENCE DESCRIPTION: SEQ ID NO:25:

| AGCTAGATTA | AGTAANATAT | AGAATATGGT | ATAATTTATT | GATGTATANC | CCAANACAAT | 60 |
|---|---|---|---|---|---|---|
| TTATATATTT | TTTCAATCAT | TNNAAATATA | TATTTAATAN | TGCTTTATGG | TATTATGATA | 120 |

```
TGGTNNCNNA AATAGAACAT AAAAGGAGCA TGGTAAGTGG CTAAACTCGA TCAAACAAAA    180

ACCCCATTTT TTGATAAAAT TAGAGCATAT GGAGTCTCAG GANCGNCGGC TTTAGATGTT    240

CCTGGTCATA AACTGGGTTC GATTGATAAT GAATTTACAA GATATTTAGG ACATAACGTT    300

TTTTCT ATG GAT NCA AAT GCA CCA AGA GGA CTT GAT AAT TTA TCN AAA      348
       Met Asp Xaa Asn Ala Pro Arg Gly Leu Asp Asn Leu Xaa Lys
        1           5                       10

CCT AAA GGT GTC ATT AAG GAA GCA CAA GCA CTC GCA GCA GAT GCT TTT     396
Pro Lys Gly Val Ile Lys Glu Ala Gln Ala Leu Ala Ala Asp Ala Phe
 15              20                  25                      30

GGT GCG GAT CCC GTC GNT TT                                          416
Gly Ala Asp Pro Val Xaa
                 35
```

( 2 ) INFORMATION FOR SEQ ID NO:26:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met Asp Xaa Asn Ala Pro Arg Gly Leu Asp Asn Leu Xaa Lys Pro Lys
 1           5                       10                      15

Gly Val Ile Lys Glu Ala Gln Ala Leu Ala Ala Asp Ala Phe Gly Ala
             20                  25                      30

Asp Pro Val Xaa
             35
```

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GCTGGCGAAA GGGGGATGTG CTGCAAGGCG    30

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GACGGGATCC TTAAATACTA A    21

( 2 ) INFORMATION FOR SEQ ID NO:29:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

CGTAAGCTTC CTCCAACAAC AAAAACCTTG A    31